(12) United States Patent  
Dasbach et al.

(10) Patent No.: US 9,022,993 B2  
(45) Date of Patent: May 5, 2015

(54) DRIVE ASSEMBLY FOR A DRUG DELIVERY DEVICE AND DRUG DELIVERY DEVICE

(75) Inventors: Uwe Dasbach, Frankfurt am Main (DE); Steffen Raab, Frankfurt am Main (DE); Marianne Rottluff, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 481 days.

(21) Appl. No.: 13/509,602

(22) PCT Filed: Dec. 6, 2010

(86) PCT No.: PCT/EP2010/068916
§ 371 (c)(1),
(2), (4) Date: Sep. 24, 2012

(87) PCT Pub. No.: WO2011/069936
PCT Pub. Date: Jun. 16, 2011

(65) Prior Publication Data
US 2013/0018327 A1    Jan. 17, 2013

(30) Foreign Application Priority Data
Dec. 7, 2009   (EP) .................................... 09178215

(51) Int. Cl.
*A61M 5/00* (2006.01)
*A61M 5/315* (2006.01)
(Continued)

(52) U.S. Cl.
CPC .............. *A61M 5/3156* (2013.01); *A61M 5/24* (2013.01); *A61M 5/31555* (2013.01);
(Continued)

(58) Field of Classification Search
CPC ............. A61M 2005/3103; A61M 2005/3126; A61M 5/24; A61M 5/31555; A61M 5/3156; A61M 5/31585; A61M 3/31593; A61M 5/482
USPC .................................................. 604/207–211
See application file for complete search history.

(56) References Cited

U.S. PATENT DOCUMENTS 4,475,905 A    10/1984  Himmelstrup
2006/0229570 A1  10/2006  Lovell et al.

FOREIGN PATENT DOCUMENTS

| EP | 1875935 | 1/2008 |
| WO | 00/62847 | 10/2000 |
| WO | 2009/136209 | 11/2009 |

OTHER PUBLICATIONS

European Search Report for European App. No. 09178215, completed Aug. 9, 2010.
(Continued)

*Primary Examiner* — Kami A Bosworth
*Assistant Examiner* — Imani Hayman
(74) *Attorney, Agent, or Firm* — McDonnell Boehnen Hulbert & Berghoff LLP (57) ABSTRACT

A drive assembly for a drug delivery device is presented having a housing with a proximal end and a distal end, a drive member, and a piston rod. A longitudinal axis extends between the proximal end and the distal end and the piston rod is axially moveable relative to the housing. The piston rod has a guide track and the drive member has a guide piece disposed and movable in the guide track. The guide track is configured with at least one section which is oblique relative to the longitudinal axis and defines a displacement for dispensing a single pre-set dose of medication during a relative movement between the guide piece and the piston rod when the guide piece cooperates with the oblique section between a distal final area of the oblique section and a proximal final area of the oblique section.

15 Claims, 6 Drawing Sheets

(51) Int. Cl.
*A61M 5/24* (2006.01)
*A61M 5/48* (2006.01)
*A61M 5/31* (2006.01)

(52) U.S. Cl.
CPC ...... *A61M 5/31585* (2013.01); *A61M 5/31593* (2013.01); *A61M 5/482* (2013.01); *A61M 2005/3103* (2013.01); *A61M 2005/3126* (2013.01)

(56) References Cited

OTHER PUBLICATIONS

International Search Report for International App. No. PCT/EP2010/068916, completed Feb. 18, 2011.

International Preliminary Report on Patentability for Int. App. No. PCT/EP2010/068916, mailed Jun. 21, 2012.

DRIVE ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2010/068916 filed Dec. 6, 2010, which claims priority to European Patent Application No. 09178215.1 filed on Dec. 7, 2009. The entire disclosure contents of these applications are herewith incorporated by reference into the present application.

FIELD OF INVENTION

The present invention relates to a drive assembly suitable for a drug delivery device and a drug delivery device.

Such drug delivery devices may have an application where a user without a formal medical training needs to administer an accurate and predefined dose of a medication or drug. In particular, such devices may have an application where medication is administered on a regular or an irregular base over a short term or long term period.

BACKGROUND

EP 1 875 935 A2 discloses an automatic injection device.

SUMMARY

It is an object of the invention to provide a drive assembly which provides improved operability. It is a further object of the invention to provide a drug delivery device which is simple to use and enables a precise delivery of the drug.

This object is achieved by a drive assembly according to claim 1 and a drug delivery device according to claim 14. Advantageous embodiments are subject matter of the dependent claims.

According to a first aspect, a drive assembly suitable for a drug delivery device comprises a housing. The housing comprises a proximal end and a distal end. A longitudinal axis extends between the proximal end and the distal end. The drive assembly further comprises a drive member (rotation sleeve). The drive assembly comprises a piston rod. The piston rod is axially moveable relative to the housing. The piston rod has a guide track. The drive member comprises a guide piece being disposed in the guide track. The guide track comprises at least one section which is oblique relative to the longitudinal axis and defines a displacement of the piston rod with respect to the housing for dispensing a single pre-set dose of medication during a relative movement between the guide piece and the piston rod when the guide piece cooperates with the oblique section between a distal final area of the oblique section and a proximal final area of the oblique section. The pitch of the at least one oblique section varies, preferably decreases, from the distal final area of the oblique section to the proximal final area of the oblique section.

The relative movement of the guide piece in the oblique section may be a movement of the guide piece in the oblique section. In further embodiments, the guide piece may be fixed and the piston rod with the oblique section moves relative to the sliding piece.

The pitch of a part of the oblique section may be the ratio of the axial distance to the distance in circumferential direction between two points on the oblique section wherein the two points form the beginning and the end of this part of the oblique section. The respective part of the oblique section may be infinitesimal.

The pitch of the oblique section varies from the distal final area to the proximal final area of the oblique section. The pitch of the oblique section may vary, preferably decrease, in a sub-section of the oblique section. Preferably, the pitch of the oblique section decreases continuously from the distal final area to the proximal final area of the oblique section. In further embodiments, the pitch of the oblique section may decrease in limited areas between the distal final area and the proximal final area and may be constant in further areas of the oblique section.

The advantage of this drive assembly is that the velocity of the injection decreases during the run of the guide piece in the current oblique section. Consequently, the injected dose of medication decreases in the end of the dose delivery phase. The dispersion period of the medication decreases due to that the injected dose of medication decreases in the end of the dose delivery phase. Therefore, the injection time as the time in which the drug delivery device effectively remains in the biological tissue of the user during the delivery of medication may be kept small. Furthermore, in the end of the dose delivery phase the compression of the bung can be kept small. Therefore, the injection stress can be kept small in the end of the dose delivery phase, and a leakage of drug from the drug delivery device may be prevented.

In an advantageous embodiment the guide track comprises at least one further section being perpendicular relative to the longitudinal axis and being designed for setting or selecting a dose of medication during the relative movement of the guide piece in the perpendicular section.

This has the advantage that a phase of setting or selecting a dose of medication prior to the dose delivery phase may be carried out. An unintentional movement of the piston rod during the phase of setting may be prevented.

In a further advantageous embodiment the guide track comprises a plurality of oblique sections and perpendicular sections. Each of the perpendicular sections is arranged between two oblique sections in a way that the guide track forms a continuous line.

This has the advantage that multi-dosing applications are possible with the drug delivery device.

In a further advantageous embodiment the oblique sections are designed to convert a movement of the drive member relative to the housing into an axial movement of the piston rod, for example by mechanical interaction between the guide piece and the piston rod in the oblique sections.

In a further advantageous embodiment the perpendicular sections are designed to prevent an axial movement of the piston rod.

In a further advantageous embodiment a further drive member is moveable relative to the housing. The further drive member may be part of the drive assembly. The drive member is in mechanical cooperation, e.g. in engagement, with the further drive member. The drive member is movable relative to the housing when the further drive member is displaced relative to the drive member. A biasing member is designed to exert a force on the further drive member in axial direction during the delivery of medication during the movement of the guide piece relative to the oblique section in the proximal final area of the oblique section.

This has the advantage that a low injection force which can lead to a higher speed of the dose button/further drive member in the end of the dose delivery phase due to the decreasing pitch of the oblique section of the guide track may be compensated by the biasing member. Consequently, the effective injection force may be kept constant during one dose delivery phase. Consequently, the user feels more comfortable during the dose delivery phase.

In a further advantageous embodiment the biasing member comprises a compression spring.

This has the advantage that a simple form of the biasing member may be used.

According to a further embodiment the further drive member is axially moveable relative to the housing. The drive member is a rotation sleeve which is in mechanical cooperation with the further drive member to be rotatable relative to the housing when the further drive member is displaced in axial direction relative to the rotation sleeve.

The rotation sleeve is arranged to be rotatable relative to the housing when the further drive member is displaced in the distal direction or in the proximal direction by mechanical interaction of the further drive member and the rotation sleeve. Preferably, the further drive member is guided axially. An axial force exerted on the further drive member, for example by a user, is transformed into a rotational movement of the rotation sleeve with respect to the housing. That force may be transformed into a distal movement of the piston rod with respect to the housing when the rotation sleeve is rotating in the first direction.

This has the advantage that a simple transformation of an axial force on the further drive member into a rotational movement of the rotation sleeve with respect to the housing is possible. Furthermore, the axial movement of the further drive member may be controlled in a very precise manner. Therefore, an exact dosing of the medication is facilitated. Furthermore, this may be very convenient for the user of the drug delivery device as there is no rotational movement of the further drive member necessary during its operation.

According to a further embodiment the piston rod is in mechanical cooperation, e.g. in engagement, with the rotation sleeve to be moveable in the distal direction relative to the housing when the rotation sleeve rotates in a first direction relative to the housing, e.g. for delivering a dose of medication. The piston rod is in mechanical cooperation with the rotation sleeve to be stationary or essentially stationary in axial direction relative to the housing when the rotation sleeve rotates in a second direction opposite to the first direction, e.g. for setting or selecting a dose of medication.

The piston rod is moveable in the distal direction relative to the housing when the rotation sleeve is rotating in the first direction and is stationary in axial direction relative to the housing when the rotation sleeve is rotating in the second direction relative to the housing opposite to the first direction.

The advantage of this drive assembly is that due to the axial movement of the piston rod relative to the housing a very high mechanical stability of the piston rod relative to the rotation sleeve can be achieved. Consequently, a very high mechanical stability of the drive assembly may be achieved.

According to a further embodiment the oblique section is designed to convert a rotational movement of the rotation sleeve in the first direction into an axial movement of the piston rod.

According to a further embodiment the perpendicular sections have an extension perpendicular to the longitudinal axis which limits the rotational movement of the rotation sleeve.

According to a further embodiment the guide track and the guide piece are designed to cooperate as a slotted guide.

This has the advantage that the guide track and the guide piece can be simply designed to cooperate as a slotted guide which allows a good guiding of the piston rod relative to the rotation sleeve.

According to a further embodiment the guide track forms a zigzag-like line on an outer surface of the piston rod. The zigzag-like line extends in axial direction.

According to a second aspect a drug delivery device comprises a drive assembly according to the first aspect. The drug delivery device comprises a medication containing cartridge. The medication containing cartridge is coupled to the piston rod in a manner to dispense the medication.

Medication and drug are used as equivalent expressions in this context.

The terms "drug" and "medication", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Exemplary embodiments of the invention are explained in the following with the help of schematic drawings. These are as follows.

DETAILED DESCRIPTION

Figure 1:
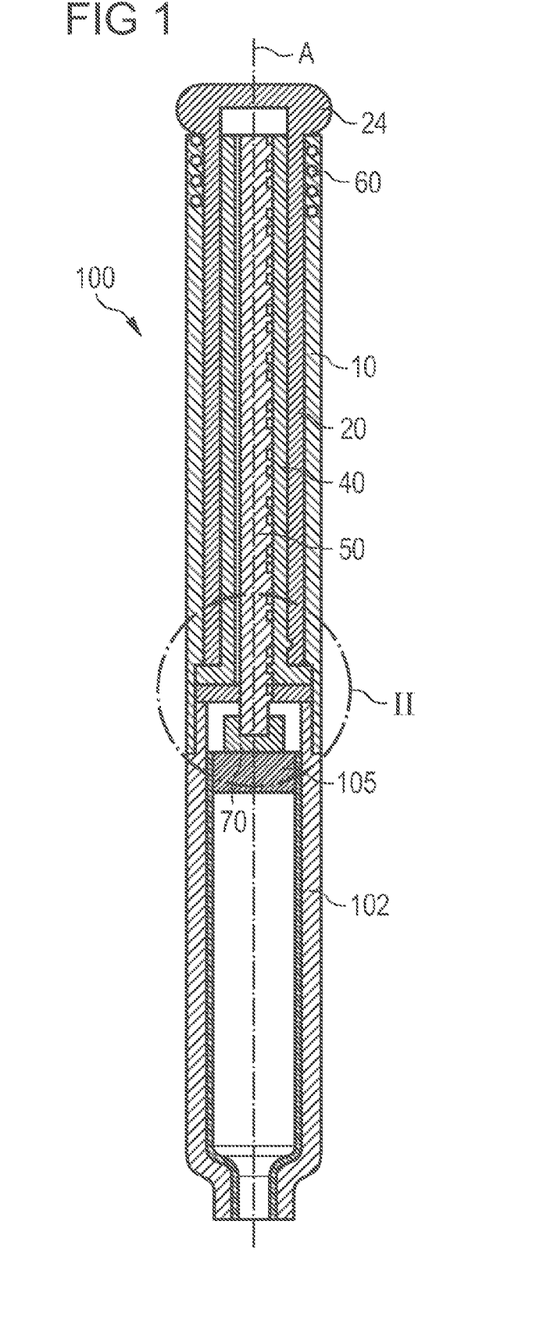
FIG. 1 schematically shows a drug delivery device with a drive assembly according to an embodiment in a longitudinal section view, FIG. 2 schematically shows a detail of the drug delivery device with the drive assembly according to an embodiment in a longitudinal section view, FIG. 3 schematically shows parts of the drive assembly according to an embodiment in a perspective view, FIG. 4 schematically shows a section of the piston rod according to an embodiment in a plan side view, FIG. 4A schematically shows a section of the piston rod according to a further embodiment in a plan side view, FIG. 4B schematically shows a section of the piston rod according to a further embodiment in a plan side view, FIG. 4C schematically shows a section of the piston rod according to a further embodiment in a plan side view, FIG. 4D schematically shows a section of the piston rod according to a further embodiment in a plan side view, FIG. 5 schematically shows a part of the drug delivery device, and FIG. 6 schematically shows a drug delivery device.
Figure 2:
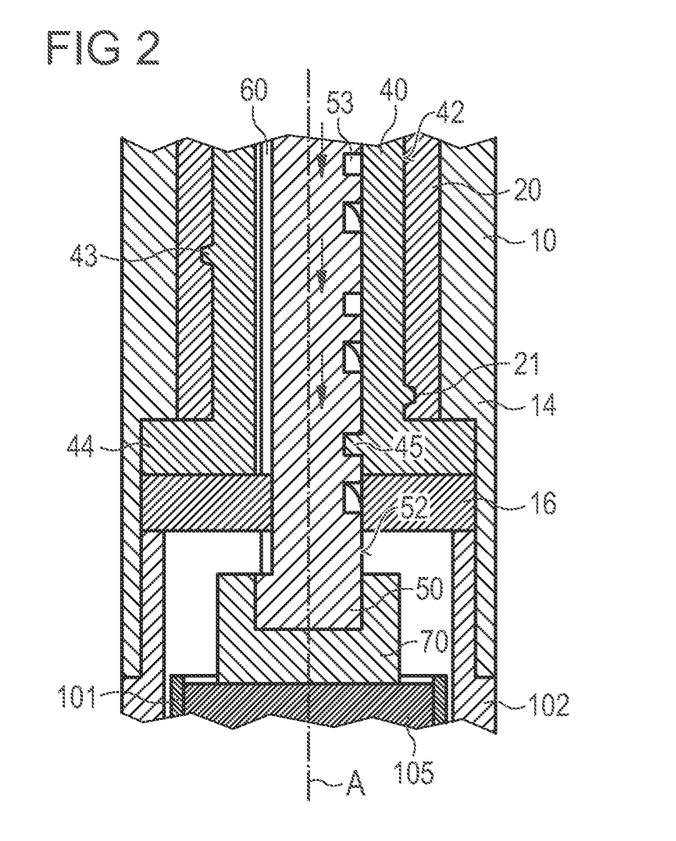
Figure 6:
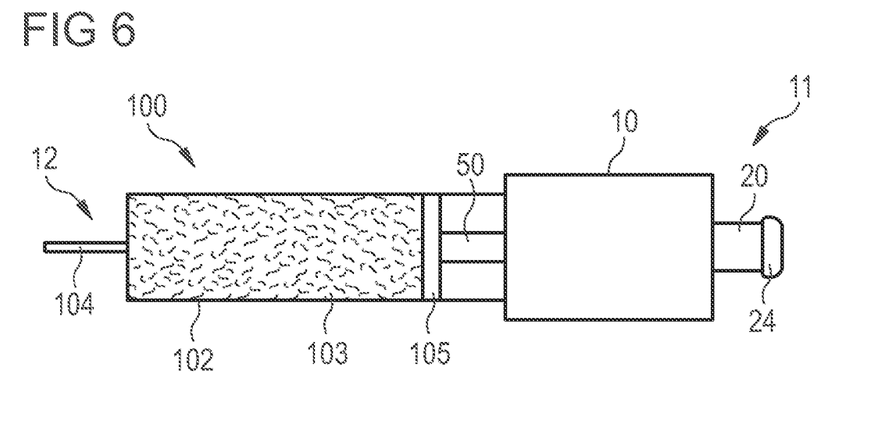

FIGS. 1, 2 and 6 show a drug delivery device 100 with a drive assembly. Preferably, the drug delivery device 100 is a pen-type drug delivery device which may inject drugs. Preferably, the drug delivery device 100 is a fixed dose device, in particular a device for dispensing fixed, non user-variable, for example constant, doses. The drug delivery device 100 comprises a medication containing cartridge 101 which is arranged in a cartridge holder 102. The cartridge 101 holds a medication 103. The drug delivery device 100 further comprises a needle device 104. The needle device 104 is arranged at the distal end of the cartridge holder 102 and is preferably secured to it. The medication 103 may be dispensed through the needle device 104. The medication 103 may comprise insulin, growth hormones, low molecular weight heparins, and/or their analogues and/or derivatives. The medication 103 may be a fluid.

A bung 105 is arranged inside the cartridge 101. The bung 105 is capable of being displaced inside the cartridge 101. A displacement of the bung 105 in the distal direction relative to the cartridge 101 results in a dispensing of medication. The movement of the bung 105 is actuated by a piston rod 50. The piston rod acts on the bung 105 via a bearing 70. Preferably, the bearing 70 is axially arranged between the piston rod 50 and the bung 105. Alternatively, the bearing 70 may be dispensed with.

At the proximal end of the medication containing cartridge 101, the drive assembly is arranged. The medication containing cartridge 101 is preferably secured to a housing 10 at the distal end side of the housing 10.

Figure 5:
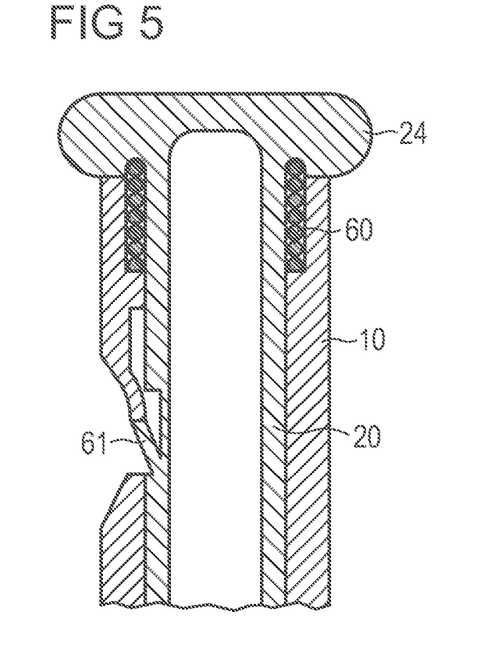

The drive assembly comprises the housing 10. Furthermore, the drive assembly comprises a drive member 40 and a further drive member 20. Preferably, the drive member 40 is a rotation sleeve. Furthermore, the drive assembly comprises the piston rod 50. Additionally, the drive assembly comprises a biasing member 60 which is preferably arranged between the further drive member 20 and the housing 10. The biasing member 60 may exert a force on the further drive member 20 in axial direction during the delivery of medication. Preferably, the biasing member 60 comprises a compression spring. As can be seen in the embodiment of FIG. 5, the drive assembly may comprise a snap-in member 61 which is preferably arranged between the further drive member 20 and the housing 10 to prevent an undesired axial movement of the further drive member 20.

Preferably, the housing 10 extends between a proximal end 11 and a distal end 12. The housing 10 may have a hollow cylindrical shape. Preferably, the housing 10 comprises a first section 14 and a second section 16. The first section 14 is shaped like a sleeve. The second section 16 is shaped like a disk. The second section 16 is fixedly coupled to the first section 14.

The housing 10 may comprise coupling means arranged at the distal end 12. The coupling means on the distal end 12 may be for coupling the housing 10 with the cartridge holder 102. The cartridge holder 102 interacts with the second section 16. The second section 16 acts as an intermediate element for the cartridge holder 102 to obtain a defined position of the cartridge holder 102.

A longitudinal axis A extends between the proximal end 11 and the distal end 12. The longitudinal axis A basically extends through the center of the housing 10. The surfaces of the housing 10 basically extend along the longitudinal axis A. The housing 10 may comprise an opening, for example to provide a display which may show the number of dispensed or remaining doses of drug.

The further drive member 20 preferably comprises an inner thread 21 which is extending in axial direction (FIG. 2). The inner thread 21 of the further drive member 20 follows a helical path with a centre axis of this path being the longitudinal axis A or an axis parallel to the longitudinal axis A. In alternative embodiments, the rotation sleeve has an outer thread which engages with an engaging device of the further drive member 20. The further drive member 20 is axially displaceable with respect to the housing 10 and thereby enables a rotational movement of the rotation sleeve via the thread 21. Preferably, any axial movement of the further drive member 20 relative to the rotation sleeve is converted into a rotational movement of the rotation sleeve.

The further drive member 20 is preferably splined to the housing 10. The further drive member 20 preferably comprises at least one groove which is extending in axial direction. The groove is in engagement with the housing 10 for example with a tab. The tab is a part of the housing 10 or is locked to the housing 10. The groove being in engagement with the housing 10 may ensure an axial movement of the further drive member 20 relative to the housing 10. In alternative embodiments, the housing 10 comprises a groove and the further drive member 20 has a tab being in engagement with the groove.

The further drive member 20 preferably comprises coupling means for coupling the further drive member 20 with further elements. For example, a dose button 24 is coupled to the further drive member 20. The dose button 24 may transfer a force exerted on the dose button 24 in distal or proximal direction to the further drive member 20. The dose button 24 may be pushed in the distal direction with respect to the housing 10 for administering a dose of medication. The dose button 24 may be pulled in the proximal direction with respect to the housing 10 for setting a dose of medication. In particular, the dose button 24 may be pulled in the proximal direction with the support of the biasing member 60. In another embodiment the force for administering a dose of medication is exerted directly on the further drive member 20. In this embodiment no separate dose button 24 is needed. The force may be a force being exerted manually on the dose button 24 by a user.

Figure 3:
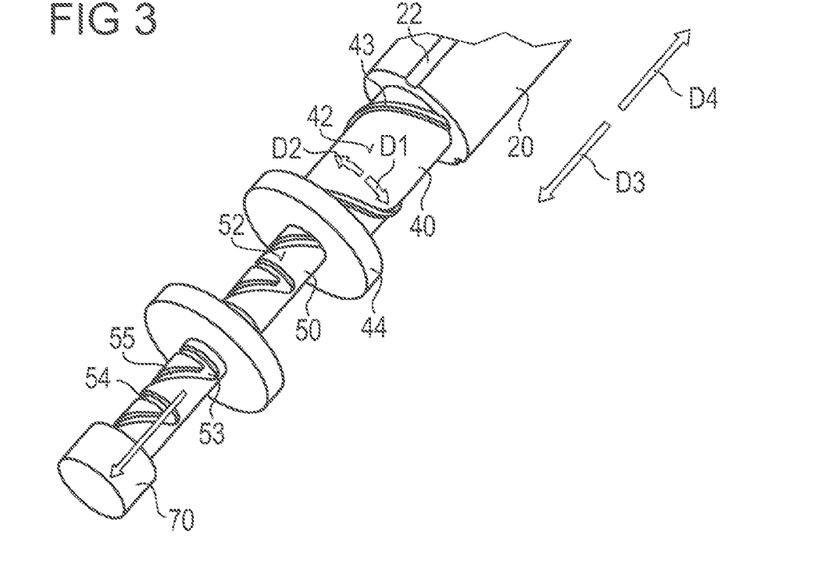

The rotation sleeve has an outer surface 42. The outer surface 42 comprises an engaging device 43 which extends in axial direction and is in engagement with the thread 21 of the further drive member 20. The thread 21 and the engaging device 43 enable a transformation of an axial movement of the further drive member 20 into a rotational movement of the rotation sleeve. A rotational movement of the rotation sleeve can be carried out in a first direction D1 or in a second direction D2 which is counterclockwise to the first direction D1 (FIG. 3). In particular, a rotational movement of the rotation sleeve in the first direction D1 can be achieved by a movement of the further drive member 20 in a distal direction D3 relative to the housing 10 which is a distal movement of the further drive member 20. Accordingly, a rotational movement of the rotation sleeve in the second direction D2 can be achieved by an axial proximal movement of the further drive member 20 relative to the housing 10 in a proximal direction D4.

The rotation sleeve further comprises a protrusion 44 extending in radial direction, e.g. a radially outwardly directed flange. As the protrusion 44 is arranged in axial direction between the first section 14 and the second section 16 of the housing 10 (see FIG. 3) an axial movement of the rotation sleeve relative to the housing 10 may be prevented.

Therefore, the rotation sleeve carries out a rotational movement in the first direction D1 and in the second direction D2 only.

The drive member 40 has a guide piece 45 protruding from an inner surface of the drive member 40 in radial direction, in particular towards the longitudinal axis A of the housing 10. The guide piece 45 is in engagement with the piston rod 50.

The piston rod 50 has an outer surface 52. A guide track 53 is arranged on the outer surface 52 of the piston rod 50. Preferably, the guide piece 45 of the drive member 40 is arranged in the guide track 53. Preferably, the guide piece 45 is moveable in the guide track 53. The engagement of the guide piece 45 and the guide track 53 enables a secure slotted link between the drive member 40 and the piston rod 50.

Figure 4:
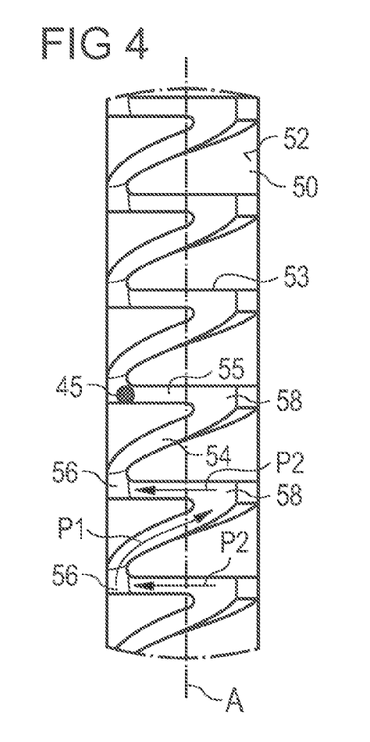
Figure 4A:
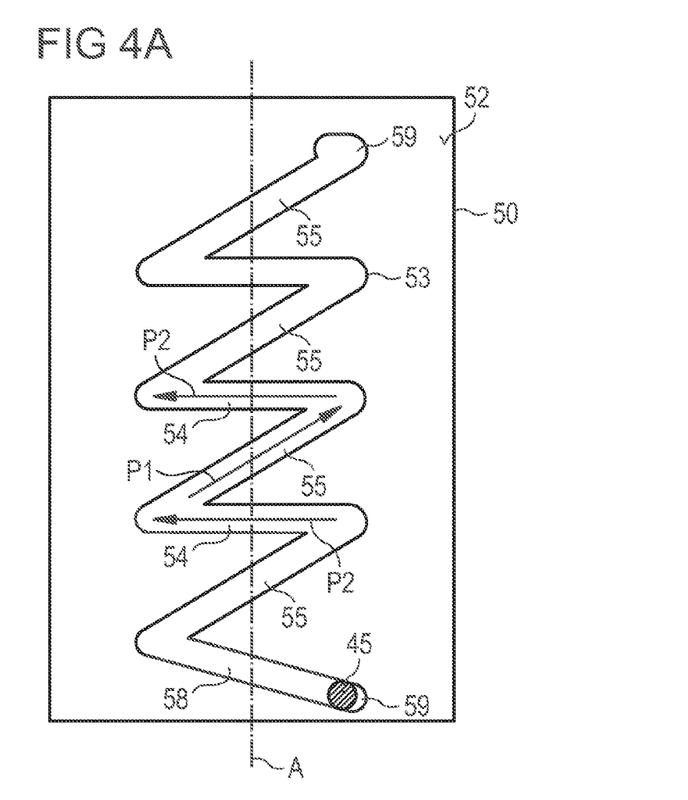

Preferably, the guide piece 45 has a circular square section, as shown in FIGS. 4 and 4A. This allows a smooth and secure movement of the guide piece 45 in the guide track 53.

FIG. 4 shows the guide track 53 of the piston rod 50 in a detailed view. The guide piece 45 and the guide track 53 are engaged. The guide track 53 runs on the outer surface 52 of the piston rod 50 which may be curved. For illustrating the function of the rotation sleeve and the piston rod 50 the path of the guide track 53 is shown in plan view in FIG. 4. The guide track 53 may be moved along the guide piece 45 when the piston rod 50 is moved in the distal direction.

Figure 4B:
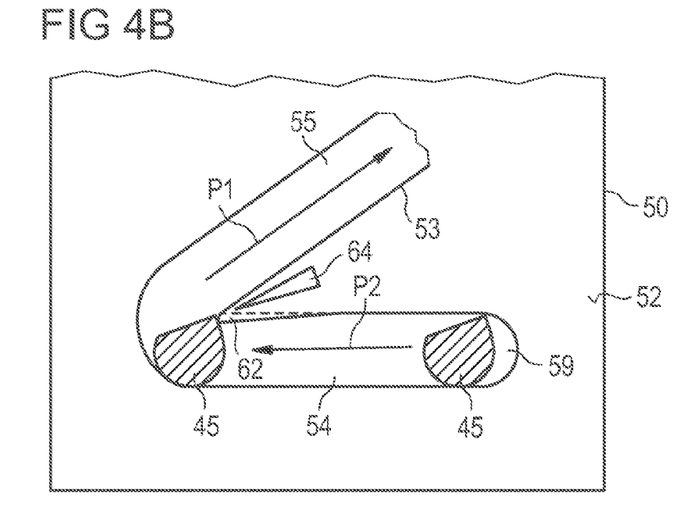

As can be seen particularly in FIGS. 4, 4A and 4B, the guide track 53 is preferably formed as a zigzag-like line on the outer surface 52 of the piston rod 50. Preferably, the zigzag-like line is extending in axial direction, in particular as far as a main direction of extent of the guide track 53 is concerned.

Figure 4C:
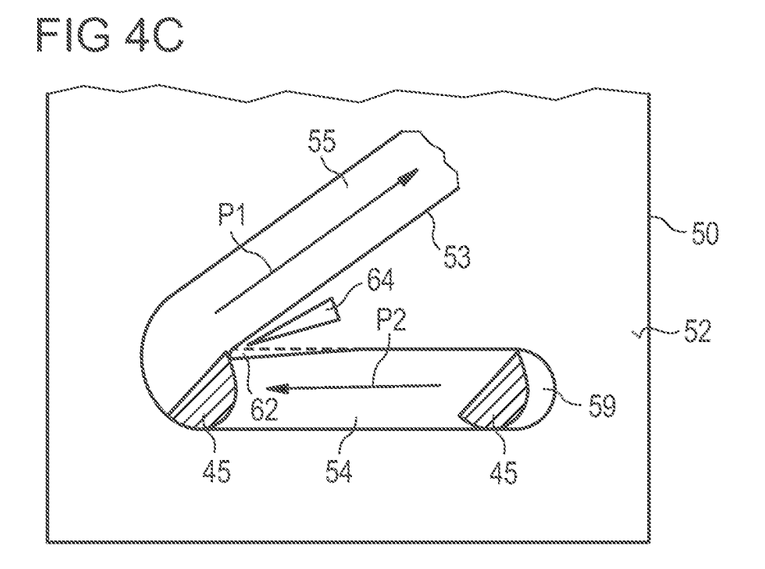
Figure 4D:
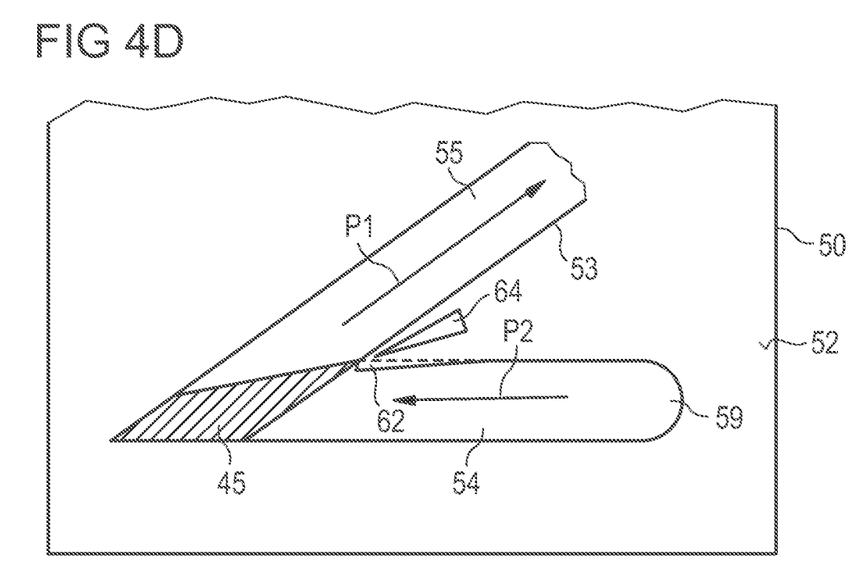

The guide track 53 has consecutive segments. Each of the consecutive segments of the guide track 53 comprises an oblique section 54. Furthermore, each of the consecutive segments of the guide track 53 comprises a perpendicular section 55. Each of the consecutive segments of one of the oblique sections 54 and one of the perpendicular sections 55 is formed like a "V". A single of these consecutive segments formed as a "V" is shown in FIGS. 4B, 4C and 4D.

The perpendicular sections 55 extend expediently perpendicular or essentially perpendicular relative to the longitudinal axis A and are acting as dose setting sections. The guide piece 45 travels in the perpendicular sections 54 during dose setting.

The oblique sections 54 extend obliquely relative to the longitudinal axis A and are acting as dose dispensing sections. If the section 55 of a segment is oblique with respect to the axis A, the section 54 of that segment is preferably more oblique with respect to the axis A. It is, however, preferred that the sections 55 extend perpendicular with respect to the axis A. The guide piece 45 travels in the oblique sections 54 during dose dispensing. The oblique sections 54 define first paths P1, and the perpendicular sections 55 define second paths P2. The first paths P1 and the second paths P2 are designed to guide the guide piece 45. In general, the oblique sections 54 and the perpendicular sections 55 are alternatingly disposed along the guide track 53 thereby forming the zigzag-like line for the guide track 53.

The oblique section 54 has a distal final area 56 and a proximal final area 58. The course of the pitch of the oblique section 54 is that it decreases from the distal final area 56 to the proximal final area 58. That means that the oblique section 54 forms a concave function with respect to the representation in FIG. 4. Preferably, the pitch of the oblique section 54 decreases continuously from the distal final area 56 to the proximal final area 58. In further embodiments, the pitch of the oblique section 54 may decrease in limited areas between the distal final area 56 and the proximal final area 58.

Preferably, the piston rod 50 is splined to the housing 10. This facilitates a precise movement of the piston rod 50 in the axial direction without a rotation.

In the embodiment of FIG. 4A, an end section 59 is arranged directly at the proximal end of the uppermost second section 54 relative to FIG. 4A. This makes it possible to prevent already a further setting movement of the piston rod 50 immediately after the last allowed dose has been dispensed. In the embodiment of FIG. 4, a subsequent dose setting movement is allowed, whereas the subsequent dose dispensing movement which would have to be performed is prevented.

In the embodiment of FIGS. 4B and 4C the guide piece 45 has a quasi-circular square section with an oblique cut at its proximal end. The angles of the oblique cuts are different in FIGS. 4B and 4C. The oblique cut allows a smooth and secure movement of the guide piece 45 in the guide track 53.

In the embodiment of FIG. 4D the guide piece 45 has a quadrilateral square section. This shape of the guide piece 45 allows a secure movement of the guide piece 45 in the guide track 53.

Furthermore, in the embodiment of FIGS. 4B, 4C and 4D the first section 55 of the guide track 53 has a wedge-shaped projection 62 extending from the proximal wall of the perpendicular section 55. The projection 62 may be elastically deformable. The projection 62 reduces the square section, in particular the axial extension of the perpendicular section 55. The perpendicular section 55 may taper in the direction from the right to the left in view of FIGS. 4B, 4C and 4D. The projection 62 is in mechanical cooperation with the guide piece 45. The shape of the guide piece 45 of FIGS. 4B, 4C and 4D in combination in particular with the wedge-shaped projection 62 may prevent an unintended backward movement of the guide piece 45 in the guide track 53. The reason for this is that after the guide piece 45 has passed the projection 62 during its movement from the perpendicular section 55 to the oblique section 54 the shape of the guide piece 45 with its upper right edge and the shape of the projection 62 result in that the guide piece 45 snaps into the oblique section 54 and therefore prevent a movement of the guide piece 45 from the oblique section 54 back to the perpendicular section 55.

Additionally or alternatively, in the embodiment of FIGS. 4B, 4C and 4D a recess 64 is arranged between the perpendicular section 55 and the oblique section 54 adjacent to the projection 62. The recess 64 increases the flexibility of the projection 62 in the case that the guide piece 45 passes the projection 62 during its movement from the perpendicular section 55 to the oblique section 54. Consequently, a reliable passing of the guide piece 45 from the perpendicular section 55 to the oblique section 54 is possible without an interference of the prevention of the movement of the guide piece 45 from the oblique section 54 back to the perpendicular section 55.

In the following, the function of the drive assembly and the drug delivery device according to the embodiment of FIG. 4 will be described in detail:

An actuation of the dose button 24, preferably a manually actuated movement of the dose button 24 with respect to the housing 10, causes linear displacement of the further drive member 20 which is part of the drive assembly. The further drive member 20 is linearly displaced in the distal direction, for example towards the distal end 12, and the needle device 104 respectively. The linear displacement of the further drive member 20 causes a rotational movement of the rotation sleeve in one of the first or second directions D1, D2 and a corresponding displacement of the piston rod 50.

During a setting of the dose, the user removes the snap-in element 61 and pulls the further drive member 20 in the proximal direction D4. This movement may be supported by the biasing member 60. As the movement of the further drive member 20 in the proximal direction D4 relative to the housing 10 is correlated with a rotational movement of the rotation sleeve in the second direction D2, the guide piece 45 of the rotation sleeve travels along the perpendicular section 55 of the guide track 53 on the second path P2 from the proximal final area 58 of the preceding oblique section 55 to the distal final area 56 of the subsequent oblique section 55. The movement of the guide piece 45 is restricted by two walls limiting the guide track 53. The guide piece 45 travels along the second path P2 until the guide piece 45 comes into contact with a wall of the guide track 53, e.g. a wall at the left of the guide track 53, near or in the distal final area 56 between the perpendicular section 55 and the oblique section 54 of the current segment of the guide track 53. The piston rod 50 can not move in axial direction relative to the housing 10 during the dose setting process. At the end of the second path P2 in the distal final area 56 of the subsequent oblique section 55 the dose setting process is completed.

For dispensing the dose, the user pushes the further drive member 20 of the drug delivery device 100 in the distal direction D3. Preferably, the movement of the further drive member 20 in the distal direction D3 is terminated when the snap-in element 61 comes into engagement with the housing 10 as shown in FIG. 5. As the movement of the further drive member 20 in the distal direction D3 relative to the housing 10 is correlated with a rotational movement of the rotation sleeve in the first direction D1, the guide piece 45 of the rotation sleeve follows the first path P1 of the oblique section 55 from the distal final area 56 to the proximal final area 58. The movement of the guide piece 45 is again restricted by the two walls limiting the guide track 53. The guide piece 45 now cooperates with the wall right of the guide track 53. Therefore, the guide piece 45 travels along the first path P1 until the guide piece 45 reaches the proximal final area 58 between the oblique section 54 of the current segment and the perpendicular section 55 of a subsequent segment of the guide track 53.

During this movement, the piston rod 50 is moved in distal direction due to the guide piece 45 interacting with the wall of the oblique section 54. Thereby, medication 103 may be dispensed from the medication containing cartridge 101. As the pitch of the oblique section 54 decreases from the distal final area 56 to the proximal final area 58 of the current oblique section 54 the velocity of the injection decreases during the run of the guide piece 45 in the current oblique section 54. By this, the injection stress in the end of the dose delivery phase decreases. The dispersion period of the medication decreases due to that the injected dose medication decreases in the end of the dose delivery phase. Thus, the time in which the drug delivery device remains in the biological tissue of the user during the dosing of medication may be kept small. Furthermore, a leakage of drug from the drug delivery device in the end of the dose delivery phase may be prevented. Due to the decreasing velocity of the injection during the dose delivery phase the injection force may decrease simultaneously. As the biasing member 60 exerts a force on the further drive member 20 the decreasing injection force may be compensated by the biasing member 60 and the effective injection force may be kept constant.

After a cycle of setting and dispensing a dose as described has been carried out, a user may carry out the described steps of setting and dispensing a dose in consecutive steps, wherein the guide piece 45 of the rotation sleeve is guided by the consecutive segment with one of the oblique sections 54 and one of the perpendicular sections 55. Thus, multiple doses of a medication may be dispensed.

The invention claimed is:

1. A drive assembly for a drug delivery device, comprising:
   a housing with a proximal end and a distal end, and a longitudinal axis (A) extending between the proximal end and the distal end,
   a drive member, and
   a piston rod being axially moveable relative to the housing, wherein
   the piston rod comprises a guide track, and the drive member comprises a guide piece being disposed in the guide track, and
   the guide track comprises at least one section being oblique relative to the longitudinal axis (A) and defining a displacement of the piston rod with respect to the housing for dispensing a single pre-set dose of medication during a relative movement between the guide piece and the piston rod when the guide piece cooperates with the oblique section between a distal final area of the oblique section and a proximal final area of the oblique section, and
   wherein the at least one oblique section has a pitch that varies from the distal final area to the proximal final area.

2. The drive assembly according to claim 1, wherein the pitch of the at least one oblique section decreases from the distal final area to the proximal final area.

3. The drive assembly according to claim 1, wherein the guide track comprises at least one further section being perpendicular relative to the longitudinal axis (A) and being designed for setting or selecting a dose of medication during the relative movement of the guide piece in the perpendicular section.

4. The drive assembly according to claim 3, wherein the guide track comprises a plurality of oblique sections and perpendicular sections, and each of the perpendicular sections is arranged between two oblique sections in a way that the guide track forms a continuous line.

5. The drive assembly according to claim 3, wherein the perpendicular section is designed to prevent an axial movement of the piston rod.

6. The drive assembly according to claim 1, wherein the oblique section is designed to convert a movement of the drive member relative to the housing into an axial movement of the piston rod.

7. The drive assembly according to claim 1, wherein a further drive member is moveable relative to the housing, and the drive member is in mechanical cooperation with the further drive member to be movable relative to the housing when the further drive member is displaced relative to the drive member, and a biasing member being designed to exert a force on the further drive member in axial direction during the delivery of medication during the relative movement of the guide piece in the oblique section in the proximal final area of the oblique section.

8. The drive assembly according to claim 7, wherein the biasing member comprises a compression spring.

9. The drive assembly according to claim 7, wherein the further drive member is axially moveable relative to the housing, and the drive member is a rotation sleeve which is in mechanical cooperation with the further drive member to be rotatable relative to the housing when the further drive member is displaced in axial direction relative to the rotation sleeve.

10. The drive assembly according to claim 9, wherein the piston rod is in mechanical cooperation with the rotation sleeve to be moveable in the distal direction relative to the housing when the rotation sleeve rotates in a first direction (D1) and to be stationary in axial direction relative to the housing when the rotation sleeve rotates in a second direction (D2) opposite to the first direction (D1).

11. The drive assembly according to claim 10, wherein the oblique section is designed to convert a rotational movement of the rotation sleeve in the first direction (D1) into an axial movement of the piston rod.

12. The drive assembly according to claim 9, wherein the perpendicular sections have an extension perpendicular to the longitudinal axis (A) which limits the rotational movement of the rotation sleeve.

13. The drive assembly according to claim 9, wherein the guide track and the guide piece are designed to cooperate as a slotted guide.

14. The drive assembly according to claim 1, wherein the guide track forms a zigzag-like line on an outer surface of the piston rod, and the zigzag-like line extends in axial direction.

15. A drug delivery device with a drive assembly according to claim 1, wherein a cartridge containing medication is coupled to the piston rod in a manner to dispense the medication.

* * * * *